United States Patent [19]
Lindegren et al.

[11] Patent Number: 5,476,005
[45] Date of Patent: Dec. 19, 1995

[54] METHOD AND APPARATUS FOR TRACING LEAKS IN VIVO OCCURRING IN AN ELECTRODE DEVICE OF AN IMPLANTED MEDICAL APPARATUS

[75] Inventors: Ulf Lindegren, Enskede; Heinz Neubauer, Jaerfaella; Hans Strandberg, Sundbyberg; Hans Schueller, Lund, all of Sweden

[73] Assignee: Siemens Elema AB, Solna, Sweden

[21] Appl. No.: 271,716

[22] Filed: Jul. 7, 1994

[30] Foreign Application Priority Data

Jul. 9, 1993 [SE] Sweden ................................. 9302385

[51] Int. Cl.⁶ .............................. A61N 1/08; G01M 3/20
[52] U.S. Cl. ............................................... 73/40; 73/40.7
[58] Field of Search ........................... 73/40, 40.7, 49.4, 73/40.5 R; 128/642; 607/27

[56] References Cited

U.S. PATENT DOCUMENTS 4,548,069 10/1985 Nousak ..................................... 73/49.5

FOREIGN PATENT DOCUMENTS 0015874 9/1980 European Pat. Off. .
9202746-5 9/1993 Sweden .

Primary Examiner—Hezron E. Williams
Assistant Examiner—Michael J. Brock
Attorney, Agent, or Firm—Hill, Steadman & Simpson

[57] ABSTRACT

A method and apparatus are disclosed for tracing leaks in vivo which occur in an electrode device, such as a pacemaker or a defibrillator, the electrode device including an electrode cable containing an elongate, flexible conductor having an exterior covered with a layer of insulation and having an interior channel. A leakage tracing device which is simple in structure, and therefore inexpensive to make, and with which one or more leaks in an electrode cable implanted in a patient is/are readily detectable, has a tubular, flexible body within an external diameter smaller than inner diameter of the interior channel of the electrode cable. The tubular body can be inserted into the electrode cable's interior channel all the way to the channel's distal end, and the proximal end of the tubular body is connected to a container for a fluid. The container is capable of producing a gauge pressure which forces fluid through the tubular body into the channel, filling the channel such that a radial fluid pressure, higher than the pressure on the exterior of the electrode cable, develops in the channel. The fluid may be a or contain a contrast agent visible in a fluoroscopic exam, so that any escaping fluid can be detected, thereby indicating the presence of a leak.

10 Claims, 2 Drawing Sheets

METHOD AND APPARATUS FOR TRACING LEAKS IN VIVO OCCURRING IN AN ELECTRODE DEVICE OF AN IMPLANTED MEDICAL APPARATUS

BACKGROUND OF THE INVENTION

1. Field of the Invention

The present invention relates to a method and device for tracing leaks in vivo in an electrode device, such as for a pacemaker or a defibrillator, the electrode device being of the type having an electrode cable containing an elongate, flexible conductor whose exterior is covered with a layer of insulation and whose interior forms a channel.

2. Description of the Prior Art

Tracing leaks in electrode devices including a cable of the type described above, which are not yet implanted in a patient, is conventionally accomplished with the aid of a compressed air device connected to the orifice of the electrode cable's interior channel. Air is then forced into the channel so a gauge pressure develops and the electrode cable is immersed in water. If the cable is defective, air seeps out of the channel through the leak(s), and air bubbles appear in the water, thereby indicating presence of the leak(s).

When an implanted system, consisting of a pacemaker and an attendant pacemaker electrode, starts producing, e.g., poor threshold values or falling values for impedance, the physician may suspect the cause to be a defective pacemaker or a leak in the electrode cable, enabling body fluids to penetrate into the channel and come into contact with any non-insulated conductor. Such a leak could develop in conjunction with the introduction of the pacemaker electrode through a vein into the patient's heart, such introduction generally being performed with the aid of a relatively stiff stylet. It is not uncommon for the stylet, during introduction into the electrode cable's interior channel or when displaced in the channel, to penetrate both the conductor, which generally forms the channel, as well as the outer layer of insulation. A leak can also develop when the insulation becomes fatigued or abraded. In fluoroscopic examination of a patient with an implanted pacemaker electrode, an experienced physician or radiologist can discern a break in a conductor. Identifying a leak in the layer of insulation is, however, impossible. After having determined that the pacemaker is not at fault, the physician was therefore left with no choice but to replace the implanted electrode cable with another, without knowing for certain whether the electrode cable's layer of insulation was defective. Such certainty was also impossible to achieve when the physician explanted the electrode device, since the cable is generally damaged in the explantation procedure.

SUMMARY OF THE INVENTION

An object of the invention is to provide a device for tracing leaks in vivo in an electrode cable of the initially described type, the tracing device having a simple structure and therefore being inexpensive to make, and the tracing device making it possible to indicate with extreme simplicity the presence of one or more leaks in an electrode cable implanted in a patient.

Another object is to provide a comparable in vivo leak tracing method.

The above object is achieved in a leak tracing device including a tubular, flexible body whose external diameter is smaller than the internal diameter of the interior channel of the cable to be tested and which can be introduced into the electrode cable's channel all the way to the channel's distal end. The device further includes a container for a fluid connected to the distal end of the tubular body. The container is capable of generating a gauge pressure which forces the fluid through the tubular body and into the channel, filling the channel such that a radial fluid pressure, higher than the pressure exerted on the exterior of the electrode cable, develops in the channel. If there is/are one or more leaks in the electrode cable's insulation, this is indicated by the escape of channel fluid, which is some form of contrast medium, through the leak(s). When the physician conducts a leakage investigation in conjunction with a fluoroscopic examination of the patient's chest area, the progress of the seepage can be monitored on the fluoroscopic screen, enabling the physician to record the location of leaks on the electrode cable.

According to a preferred embodiment of the invention, the external diameter of the tubular, flexible body is dimensioned such that a space exists between the external wall of the tubular body and the inner wall of the channel when the tubular body has been inserted into the channel. This space is fillable with the fluid.

According to the invention. a method for tracing leakage in vivo in an implanted electrode cable with a device according to the aforementioned preferred embodiment is also achieved when the tubular body is inserted into the interior channel of the cable to distal end thereof and fluid is then fed into the channel, filling the space between the body and the inner wall in such a way that a radial fluid pressure, higher than the pressure exerted on the exterior of the electrode cable, develops in the channel. In this way, rapid filling of the electrode channel can be attained with only a small amount of contrast fluid. It is important for the body to be inserted into the channel all the way to the channel's distal end. This prevents air bubbles and any dirt particles in the channel from being expelled through any leak in the layer of insulation out into the patient's body, which could be harmful to the patient. Instead, air and any dirt particles are pressed up and out of the channel as the column of fluid rises.

According to another preferred embodiment of the invention, the external diameter of the tubular, flexible body is dimensioned so closely to the inner diameter of the channel such that substantially no space exists between the tubular body's external wall and the channel's inner wall when the tubular body has been inserted into the channel.

According to the invention, a procedure for tracing leaks in vivo in an implanted electrode cable with a device according to the second preferred embodiment is also achieved when the tubular body is inserted into the interior channel of the cable to be tested all the way to the channel's distal end, and fluid is fed into the channel, the tubular body then being retracted as the channel fills with fluid ahead of the tubular body's distal end side. This filling then proceeds in such a way that a radial fluid pressure, higher than the pressure on the exterior of the electrode cable, develops in the channel. Using the described procedure, the physician can very easily limit the longitudinal extent of the column of fluid in the channel while still being able to examine the corresponding part of the electrode cable's layer of insulation for any leaks. Any air and dirt particles in the channel are pressed out between the tubular body's external wall and the channel's inner wall as fluid flows into the channel.

In an advantageous refinement of the invention, the container for the fluid is a syringe with which the fluid is forced into the tubular body and out of the tubular body into the channel. This makes it easy for the physician to control the amount of fluid fed into the channel.

DESCRIPTION OF THE PREFERRED EMBODIMENTS

Figure 1:
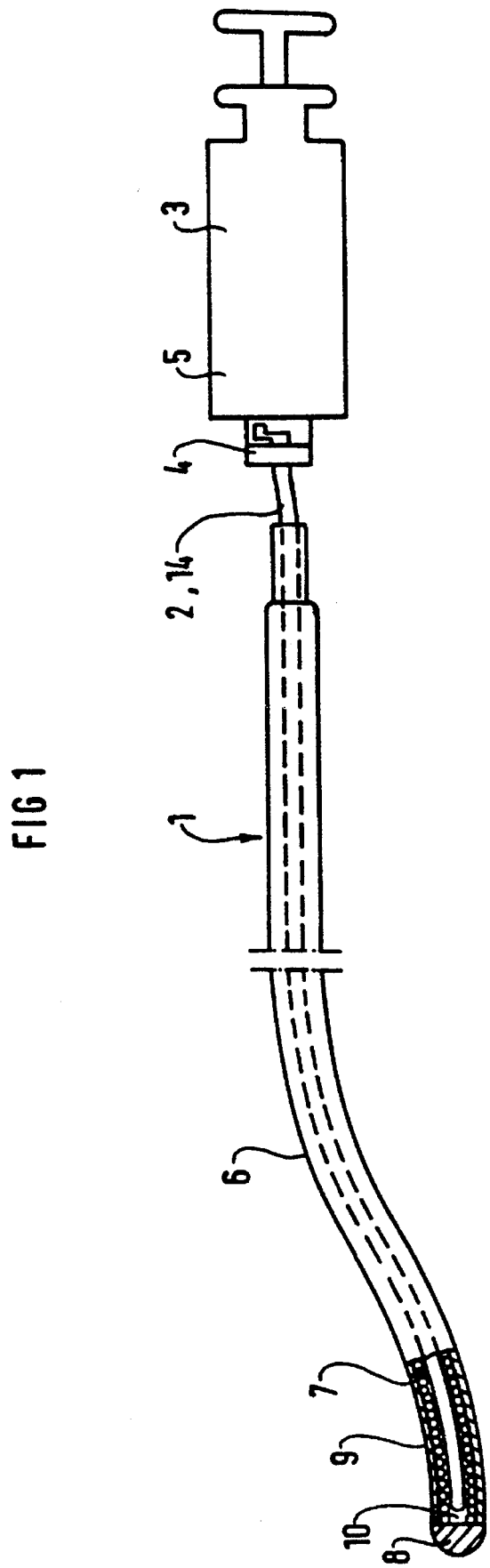
FIG. 1 shows a device, inserted into an electrode cable, for tracing leaks according to the invention.

FIG. 1 shows a device for tracing leaks in an electrode device 1, e.g., a pacemaker electrode, including a tubular, flexible body 2 whose proximal end is connected to a syringe 3 with the aid of a quick-lock 4. The syringe 3 is filled with a contrast fluid 5. The electrode device 1, which is to be examined for possible leaks in the layer of insulation, consists of an electrode cable 6 containing an elongate, flexible, helically wound conductor 7 connected to an electrode head 8 arranged on the distal end of the electrode cable 6. The exterior of the conductor 7 is provided with a layer of insulation 9, and its interior forms a channel 10. The external diameter of the body 2 is less than the inner diameter of the channel 10, so the body 2 can be inserted into the channel 10.

Before conducting an in vivo leakage investigation of the electrode device 1 implanted in a patient, a known, and therefore not shown, fluoroscopic apparatus is aimed at the patient's chest so the entire electrode cable 6 is displayed on the screen of the examination device. The experienced physician can then see the conductor 7 and the electrode head 8 of the electrode device 1.

Figure 2:
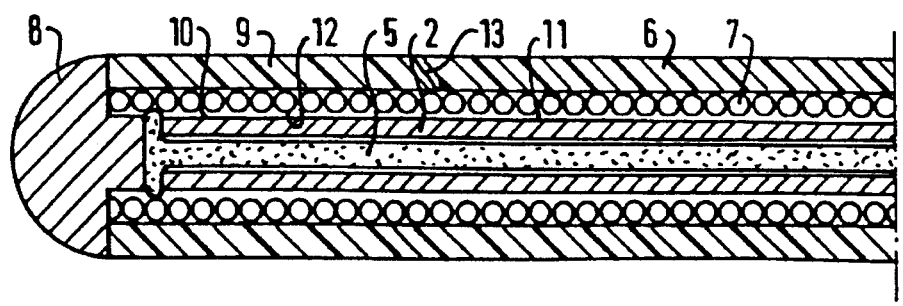
FIGS. 2–5 are side views of the distal end of the electrode cable, according to FIG. 1, in longitudinal cross-section, with devices for tracing leaks according to the invention, in respectively different positions and embodiments.
Figure 3:
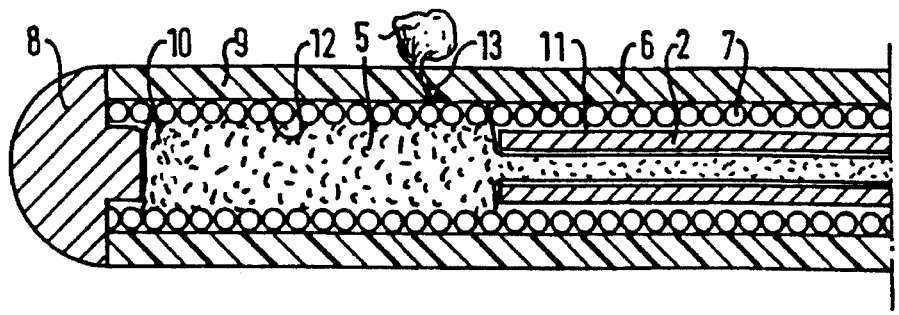

When leakage in the electrode device 1 is to be traced, the body 2 is inserted into the channel 10 all the way to the distal end of the channel 10, as shown in FIG. 1. FIG. 2, which is an enlargement of the distal end of the electrode cable 6 in longitudinal cross-section, shows that the flexible body 2 is inserted into the channel 10 until its distal end is at a distance of about one helix flight of the conductor 7 from the electrode head 8. The body 2 is also shown in FIG. 2 in longitudinal cross-section. Contrast fluid 5 is then forced, with the aid of the syringe 3, into the body 2 and out into the channel 10. FIG. 2 shows an embodiment wherein the body 2 has an external diameter dimensioned so closely to the inner diameter of the channel 10 such that contrast fluid 5 is unable to fill the very slight space between the external wall 11 of the body 2 and inner wall 12 of the channel 10 formed by the conductor 7 when the body 2 has been inserted into the channel 10. The physician then retracts the body 2 in the channel 10 as the latter fills with contrast fluid 5 ahead of the distal side of the body 2. This filling occurs in such a way that a radial fluid pressure, higher than the pressure exerted on the exterior of the electrode cable 6, develops in the channel 10. Air and any dirt particles in the channel 10 are then pressed between the external wall 11 of the body 2 and the inner wall 12 of the channel 10 by the rise in the column of contrast fluid 5. When the column of contrast fluid 5 reaches a leak 13 in the layer of insulation 9, as shown in FIG. 3, contrast fluid 5 seeps out of the leak 13. The physician, with the aid of the syringe, can control the rate at which the column of fluid 5 rises in the channel 10 and immediately detect any contrast fluid 5 seeping out of the leak 13, enabling the physician to localize and record the leak 13. The leakage examination ends when the channel 10 has become completely filled with contrast fluid 5 in the described manner.

Figure 4:
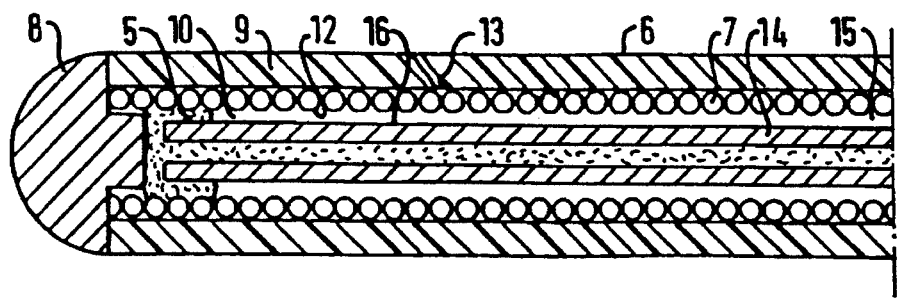

FIG. 4 shows that another embodiment of a leakage tracing body 14 can be inserted into the electrode cable 6. The external diameter of this body 14 is dimensioned such that a space 15 exists between the external wall 16 of the body 14 and the inner wall 12 of the channel 10 when the body 14 has been inserted into the channel 10. The space 15 is fillable with contrast fluid 5. This body 14 is also inserted into, the channel 10 until its distal end is at a distance of about one flight from the electrode head 8. Contrast fluid 5 then flows through the body 14 and out into the channel, in the same way described in conjunction with FIG. 2. In contrast to the previously described body 2, the body 14 can be left in the described position so a column of contrast fluid 5 forms in the space between the external wall 16 of the body 14 and the inner wall 12 of the channel 10. The column of contrast fluid pushes air and any dirt particles from the channel 10 ahead of it, and they are therefore not forced out through any leak in the layer of insulation 9. When contrast fluid 5 reaches the leak 13 in the layer of insulation 9, the contrast fluid 5 seeps out of the leak 13, as previously described. The physician can see this and record the location of the leak 13. The leakage examination ends when the space 15 in the channel 10 has become completely filled with contrast fluid 5.

Figure 5:
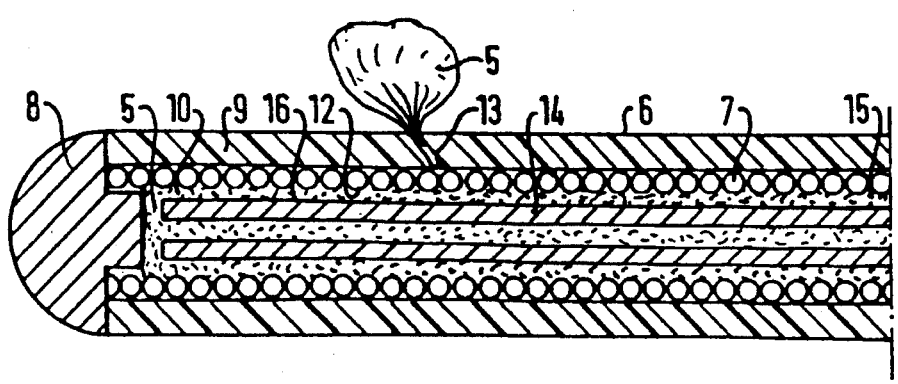

Filling of the channel 10 with contrast fluid 5 can be performed even with the body 14 shown in FIGS. 4 and 5 when the body is retracted in the channel 10 as the latter fills with contrast fluid 5. As a result: of the space 15, in which contrast fluid can flow, a distinct column of fluid is not always achieved, as is the case when a body 2, shown and described in conjunction with FIGS. 2 and 3, is employed.

A leakage examination according to the invention can clearly be used in conjunction with other types of implantable electrode devices, such as defibrillation electrodes.

Although modifications and changes may be suggested by those skilled in the art, it is the intention of the inventors to embody within the patent warranted hereon all changes and modifications as reasonably and properly come within the, scope of their contribution to the art.

We claim as our invention:

1. An apparatus for tracing leaks in vivo in an implanted electrode device, said electrode device including an electrode cable containing an elongate, flexible conductor having an extent covered by insulation, in which a leak may exist, and having an interior forming a channel having a channel diameter and a distal end, said apparatus comprising:

a tubular, flexible body having an exterior diameter smaller than said channel diameter so as to be insertable in said channel substantially to said distal end of said channel, said body having an opening communicating with said channel; and a container in fluid communication with said body and containing fluid introducible into said body and, through said opening, into said channel and said container causing said fluid in said channel to exhibit a radial fluid pressure greater than an external pressure acting on an exterior of said cable and thereby forcing said fluid through any leak which may exist in said insulation.

2. An apparatus as claimed in claim 1 wherein said channel has an inner wall defining said channel diameter and wherein said body has an exterior defining said exterior diameter, and wherein said body has an exterior diameter smaller than said channel diameter for producing a space between said exterior of said body and said inner wall of said channel when said body is inserted in said channel, said space being fillable with fluid from said container.

3. An apparatus as claimed in claim 1 wherein said body has an exterior defining said exterior diameter and wherein said channel has an inner wall defining said channel diameter, and wherein said body has an exterior diameter sufficiently close to said channel diameter so that no fluid can flow between said exterior of said body and said inner wall of said channel when said body is inserted in said channel.

4. An apparatus as claimed in claim 1 wherein said fluid comprises a contrast medium.

5. An apparatus as claimed in claim 1 wherein said container comprises a syringe.

6. A method for tracing leaks in vivo in an implanted electrode device, said electrode device including an electrode cable containing an elongate, flexible conductor having an exterior covered by insulation, in which a leak may exist, and having an interior forming a channel having a distal end, said method comprising the steps of:

inserting a flexible tubular body into said channel substantially to said distal end;

forcing fluid into said channel through said tubular body and thereby producing a radial fluid pressure in said channel which is higher than a pressure exerted on an exterior of said electrode cable; and detecting any of said fluid which escapes through said insulation due to a leak.

7. A method as claimed in claim 6 comprising the additional step of:

retracting said body from said channel as said fluid is forced into, said channel.

8. A method as claimed in claim 6 comprising the additional step of providing a tubular body having a distal end and an exterior exhibiting an exterior diameter, and said channel having an inner wall defining a channel diameter, said exterior diameter of said body being slightly smaller than said inner diameter of said channel so that no fluid can flow between said exterior of said body and said inner wall of said channel, and wherein the step of forcing fluid into said channel through said body is further defined by forcing fluid into said channel through said body exclusively between said distal end of said body and said distal end of said channel.

9. A method as claimed in claim 8 comprising the additional step of:

withdrawing said body from said channel as said fluid is forced into said channel.

10. A method as claimed in claim 6 comprising the additional step of providing a body having an exterior surface defining an exterior diameter, and wherein said channel has an inner wall defining a channel diameter, said exterior diameter of said body being smaller than said channel diameter so that a space exists between said exterior of said body and said inner wall of said channel, and wherein the step of forcing fluid into said channel through said body is further defined by forcing fluid into said space between said exterior of said body and said inner wall of said channel.

* * * * *